(12) United States Patent
Parsons et al.

(10) Patent No.: US 6,555,686 B2
(45) Date of Patent: Apr. 29, 2003

(54) ASYMMETRIC SYNTHESIS OF QUINAZOLIN-2-ONES USEFUL AS HIV REVERSE TRANSCRIPTASE INHIBITORS

(75) Inventors: Rodney L. Parsons, Wilmington, DE (US); Roberta L. Dorow, Portage, MI (US); Akin H. Davulcu, Wilmington, DE (US); Joseph M. Fortunak, Hawthorn Woods, IL (US); Gregory D. Harris, Wilmington, DE (US); Goss S. Kauffman, Bear, DE (US); William A. Nugent, Wilmington, DE (US); Lilian A. Radesca, Newark, DE (US)

(73) Assignee: Bristol-Myers Squibb Pharma, Princeton, NJ (US)

( * ) Notice: Subject to any disclaimer, the term of this patent is extended or adjusted under 35 U.S.C. 154(b) by 0 days.

(21) Appl. No.: 09/909,731

(22) Filed: Jul. 20, 2001

(65) Prior Publication Data

US 2002/0035253 A1 Mar. 21, 2002

Related U.S. Application Data

(63) Continuation-in-part of application No. 09/814,573, filed on Mar. 22, 2001, now abandoned.
(60) Provisional application No. 60/191,572, filed on Mar. 23, 2000.

(51) Int. Cl.$^7$ .................... C07D 239/72; A61K 31/517
(52) U.S. Cl. .................... 544/286; 544/283; 514/266.3
(58) Field of Search ....................... 514/266.3; 544/283, 544/286

(56) References Cited

U.S. PATENT DOCUMENTS

| 5,434,152 A | 7/1995 | Huffman et al. ......... 514/234.5 |
| 6,124,302 A | * 9/2000 | Corbett et al. ........... 514/222.5 |

FOREIGN PATENT DOCUMENTS

| WO | 9845276 | 10/1998 |

OTHER PUBLICATIONS

Tucker et al, J. Med. Chem., 1994, 37, 2437–2444.
J. Org. Chem., 1995, 60, 1590–1594, Huffman et. al.
Tetr. Letters., 1994, 35 (37) 6811–6814, Houpis et. al.
J. Org. Chem., 1998, 63, 7078–7082, Soulà et. al.

* cited by examiner

Primary Examiner—Mukund J. Shah
Assistant Examiner—Tamthom N. Truong
(74) Attorney, Agent, or Firm—Mary K. VanAtten; Gregory C. Houghton

(57) ABSTRACT

This invention relates generally to the asymmetric synthesis of quinazolin-2-ones that are useful as inhibitors of HIV reverse transcriptase. The synthesis is accomplished through the chiral ligand mediated addition of cyclopropylacetylide.

44 Claims, No Drawings

ASYMMETRIC SYNTHESIS OF QUINAZOLIN-2-ONES USEFUL AS HIV REVERSE TRANSCRIPTASE INHIBITORS

This Application is a continuation in-part application of the NON-PROVISIONAL APPLICATION Ser. No. 09/814,573, filed Mar. 22, 2001, which claims priority to PROVISIONAL APPLICATION No. 60/191,572, filed Mar. 23, 2000.

FIELD OF THE INVENTION

This invention relates generally to the asymmetric synthesis of quinazolin-2-ones that are useful as inhibitors of HIV reverse transcriptase.

BACKGROUND OF THE INVENTION

Non-nucleoside reverse transcriptase inhibitors (NNRTI's) like those of Formulas Ia and Ib shown below:

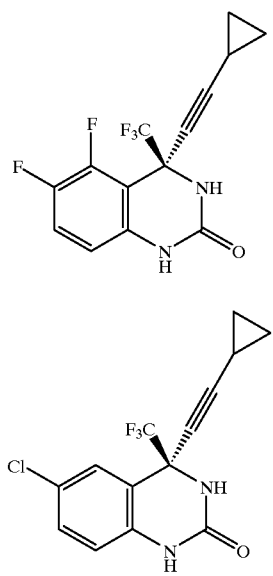

are currently being clinically investigated. As a result, large quantities of these compounds are needed to satisfy clinical demands.

Tucker et al (*J. Med. Chem.* 1994, 37, 2437–2444) describe the preparation of 4-(arylethynyl)-6-chloro-4-cyclopropyl-3,4-dihydroquinazolin-2(1H)-ones (i.e., NNRTI's) by the addition of aryl acetylides to N-protected quinazolinone precursors. A typical example is shown below.

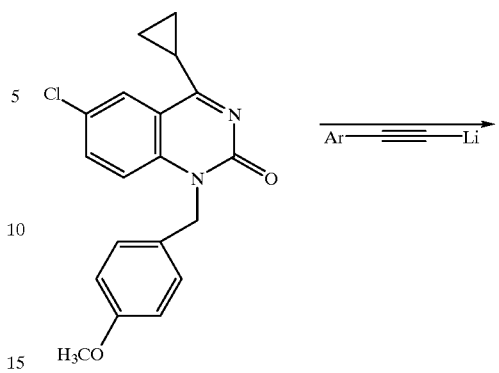

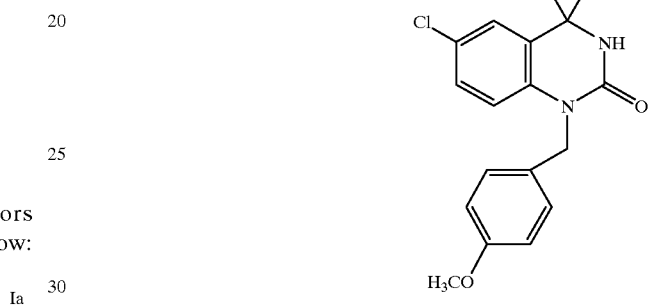

Unfortunately, the addition of the aryl acetylide requires the quinazolinone precursor to be N-protected. An undesirable deprotection step is consequently required after acetylide addition. Other papers have described similar N-protected routes (see *J. Org. Chem.* 1995, 60, 1590–1594; *Tetr. Lett.* 1994, 35(37), 6811–6814).

It can be seen that preparation of NNRTI's is difficult. Thus, it is desirable to find efficient syntheses of NNRTI'S, specifically those of Formulas Ia and Ib.

SUMMARY OF THE INVENTION

Accordingly, one object of the present invention is to provide novel asymmetric processes for preparing quinoxazin-2-ones.

These and other objects, which will become apparent during the following detailed description, have been achieved by the inventors' discovery that compounds of Formulas Ia and Ib can be prepared from quinazolinone precursors of Formulas IIa and IIb:

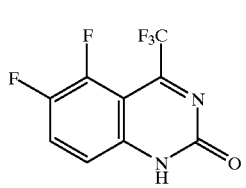

-continued

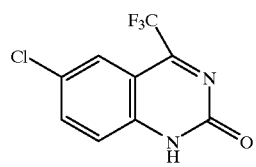
IIb via chiral moderated asymmetric addition of cyclopropylacetylene.

DETAILED DESCRIPTION OF PREFERRED EMBODIMENTS

In an embodiment, the present invention provides a novel process for making a compound of Formula Ia or Formula Ib:

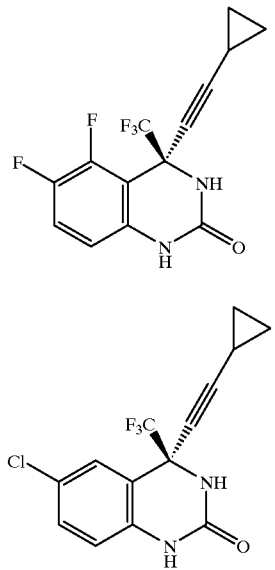

Ia

Ib comprising: contacting a quinazolinone precursor of Formula IIa or IIb:

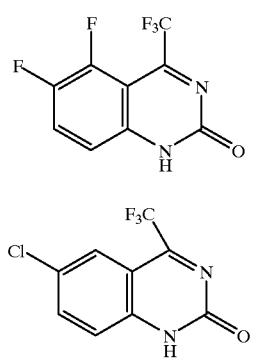

IIa

IIb with cyclopropylacetylide in the presence of a chiral moderator and a base, wherein the chiral moderator is a compound selected from:

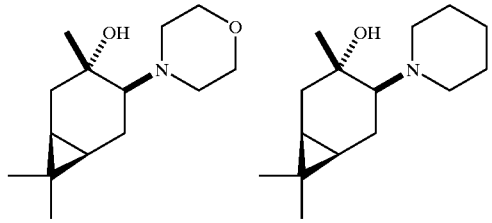

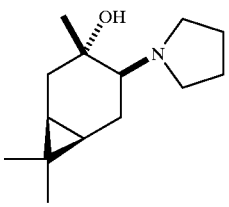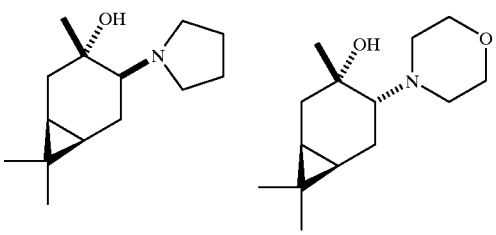

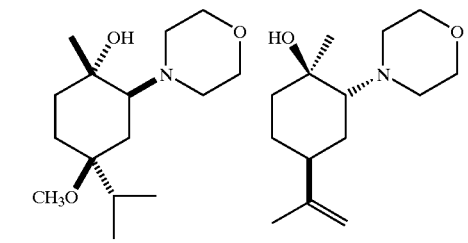

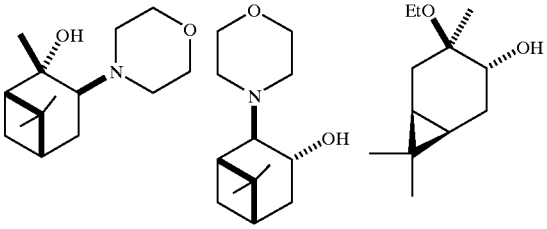

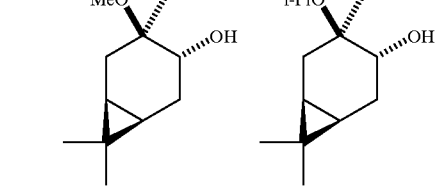

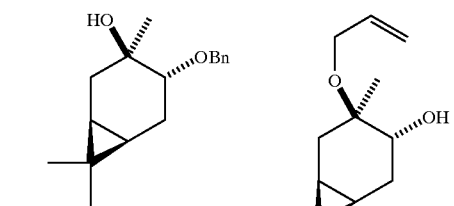

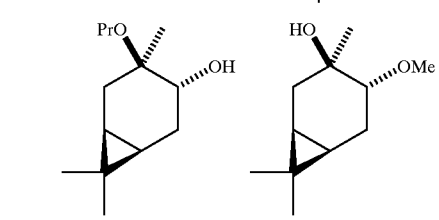

-continued
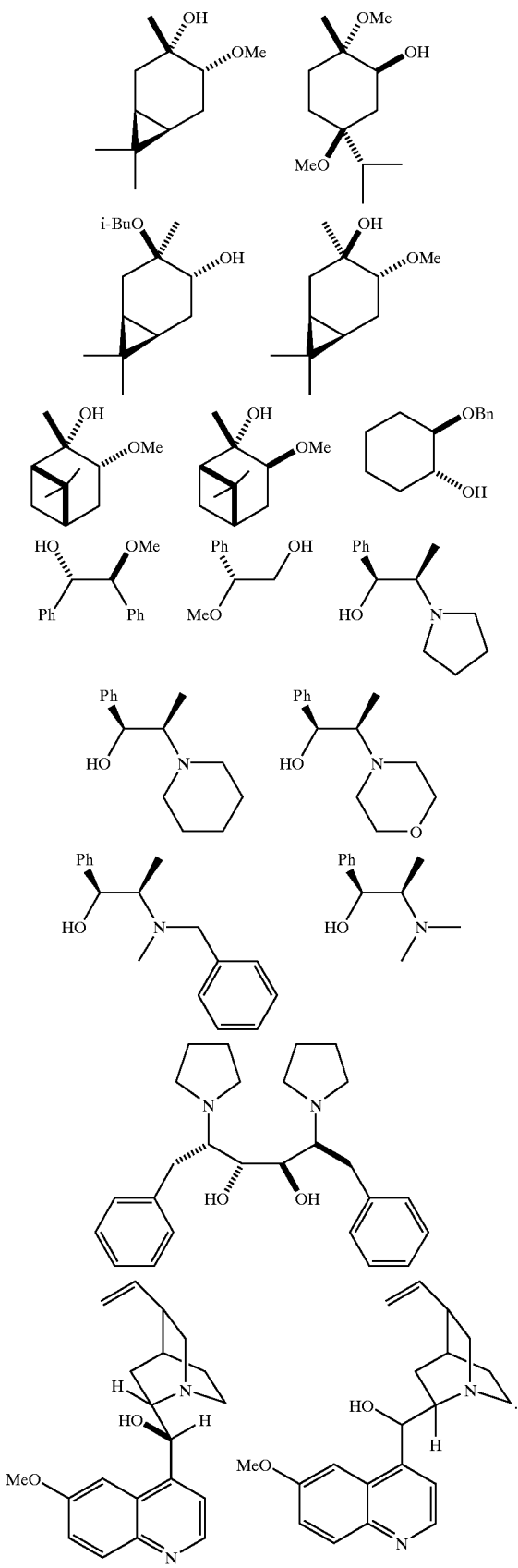
-continued
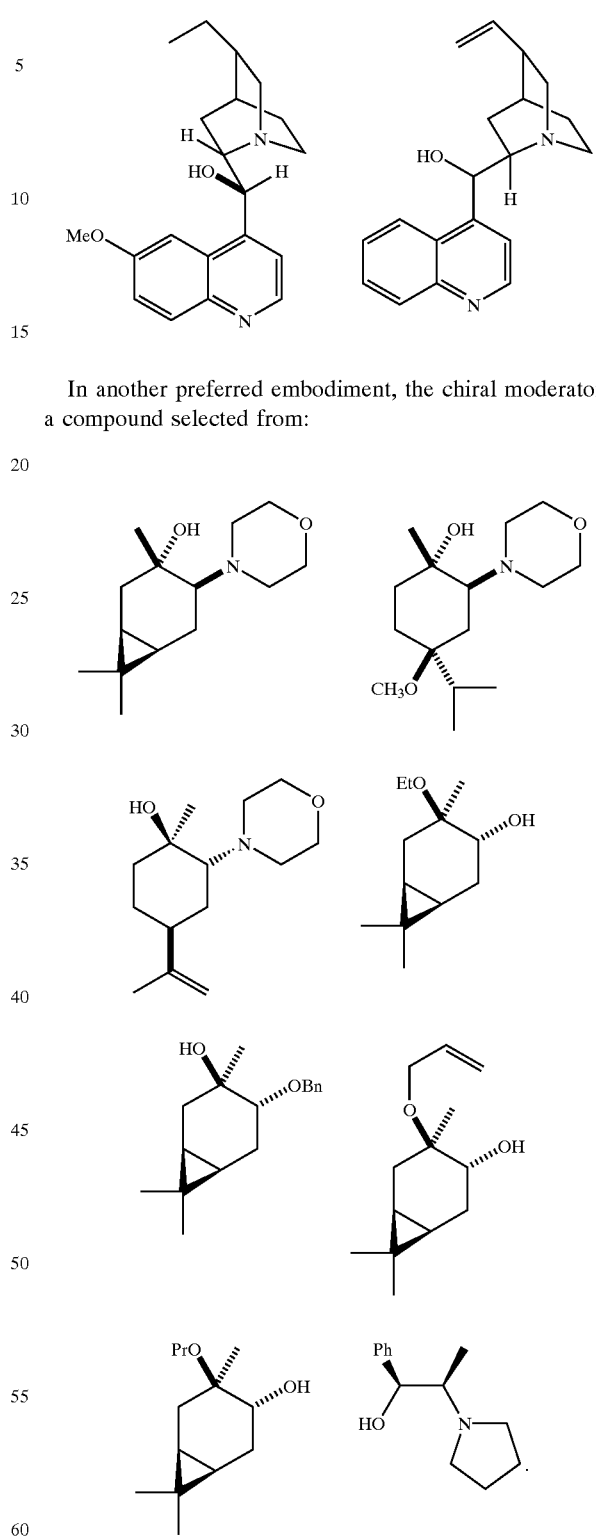
In another preferred embodiment, the chiral moderator is a compound selected from:
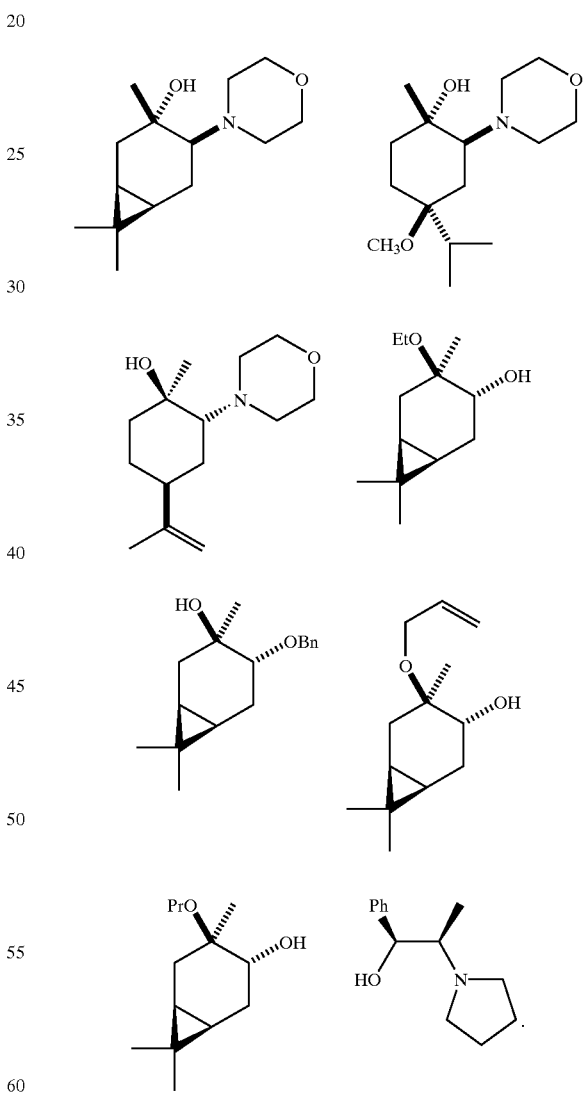
In another preferred embodiment, the chiral moderator is a compound selected from:
In another preferred embodiment, the chiral moderator (CM) is selected from:

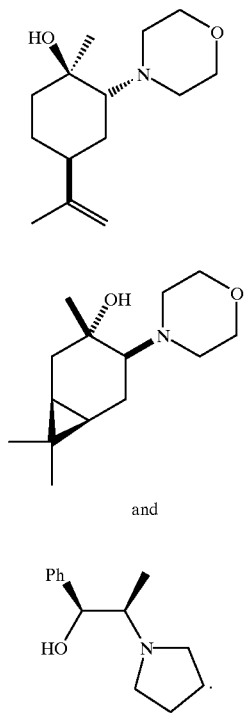

In another preferred embodiment, the chiral moderator is $CM_1$.

In another preferred embodiment, the chiral moderator is $CM_2$.

In another preferred embodiment, the chiral moderator is $CM_3$.

In another preferred embodiment, cyclopropylacetylide is lithium cyclopropylacetylide (Li-CPA).

In another preferred embodiment, contacting is performed with tetrahydrofuran as a solvent.

In another preferred embodiment, the base is selected from lithium hexamethyldisilazide, n-BuLi, s-BuLi, t-BuLi, and n-HexLi.

In another preferred embodiment, the base is n-HexLi or n-BuLi.

In another preferred embodiment, the base is lithium hexamethyldisilazide (Li-HMDS).

In another preferred embodiment, contacting is performed with tetrahydrofuran as a solvent and lithium hexamethyldisilazide as a base.

In another preferred embodiment, contacting is performed by adding a solution, comprising: a quinazolinone precursor to a solution comprising chiral moderator, Li-CPA, and base.

In a more preferred embodiment, the stoichiometric ratios are 3 to 3.6 equivalents of chiral moderator to about 3 equivalents of Li-CPA to about 6.6 equivalents of LiHMDS to 1 equivalent of quinazolinone precursor.

In another preferred embodiment, contacting is performed by adding a solution, comprising: Li-CPA, chiral moderator and base to a solution comprising quinazolinone precursor.

In another more preferred embodiment, the stoichiometric ratios are 3 to 3.6 equivalents of chiral moderator to about 3 equivalents of Li-CPA to about 6.6 equivalents of LiH-MDS to 1 equivalent of quinazolinone precursor.

In another preferred embodiment, contacting is performed by adding a solution, comprising: Li-CPA and base to a solution comprising chiral moderator and quinazolinone precursor.

In another more preferred embodiment, the stoichiometric ratios are 3 to 3.6 equivalents of chiral moderator to about 3 equivalents of Li-CPA to about 6.6 equivalents of LiH-MDS to 1 equivalent of quinazolinone precursor.

In another preferred embodiment, contacting is performed by adding a solution, comprising: chiral moderator and quinazolinone precursor to a solution comprising Li-CPA and base.

In another more preferred embodiment, the stoichiometric ratios are 3 to 3.6 equivalents of chiral moderator to about 3 equivalents of Li-CPA to about 6.6 equivalents of LiH-MDS to 1 equivalent of quinazolinone precursor.

In another preferred embodiment, contacting is performed by adding a solution, comprising: Li-CPA to a solution comprising quinazolinone precursor IIa or IIb, chiral moderator, and base. Preferably LiHMDS is used as base for this route.

In another more preferred embodiment, the stoichiometric ratios are 3 to 3.6 equivalents of chiral moderator to 1 to 1.5 equivalents of Li-CPA to 4 to 4.6 equivalents of LiHMDS to 1 equivalent of quinazolinone precursor.

In another preferred embodiment, contacting is performed by adding a solution comprising quinazolinone precursor IIa or IIb, chiral moderator, and base to a solution, comprising: Li-CPA.

In another more preferred embodiment, the stoichiometric ratios are 3 to 3.6 equivalents of chiral moderator to 1 to 1.5 equivalents of Li-CPA to 4 to 4.6 equivalents of LiHMDS to 1 equivalent of quinazolinone precursor.

In another preferred embodiment, contacting is performed by adding a solution, comprising: deprotonated chiral modifier to a solution, comprising: quinazolinone precursor and LiHMDS and then adding a solution, comprising: Li-CPA.

In another more preferred embodiment, the stoichiometric ratios are 3 to 3.6 equivalents of chiral moderator to 1 to 1.5 equivalents of Li-CPA to about 1 equivalent of LiHMDS to 3 to 3.6 equivalents of n-BuLi to 1 equivalent of quinazolinone precursor.

In another preferred embodiment, contacting is performed by adding a solution, comprising: quinazolinone precursor to a solution, comprising: a chiral modifier, cyclopropylacetylene, and LiHMDS and then adding a solution, comprising: Li-CPA.

In another more preferred embodiment, the stoichiometric ratios are about 3 equivalents of chiral moderator to about 1 equivalent of cyclopropylacetylene to 1 to 1.5 equivalents of Li-CPA to about 4 equivalents of LiHMDS to 1 equivalent of quinazolinone precursor.

In another embodiment, the quinazolinone precursor of Formula IIa or IIb:

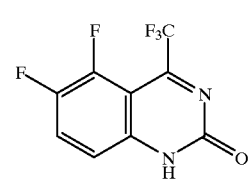

IIa

-continued

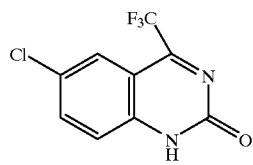
IIb is prepared by the process, comprising: dehydrating a compound of Formula IIIa or IIIb:

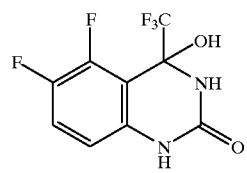
IIIa

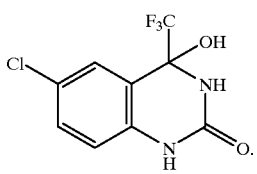
IIIb

In another preferred embodiment, dehydrating is performed by heating a compound of Formula IIIa or IIIb in a solvent selected from toluene and xylenes and mesitylenes in the presence of a water scavenger.

In another preferred embodiment, dehydrating solvent is xylenes, the water scavenger is a Dean-Stark trap, and the reaction is conducted in the presence of benzene sulfonic acid.

In another embodiment, dehydrating solvent is mesitylene, with or without the water scavenger as a Dean-Stark trap.

In another preferred embodiment, the reaction solution resulting from dehydration is reduced in volume and used in the contacting reaction without further purification.

In another embodiment, the present invention provides a novel process for making a compound of Formula Ia or Formula Ib:

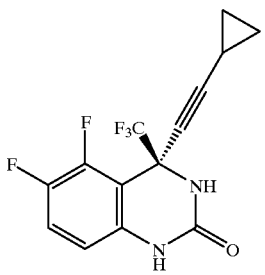
Ia

-continued

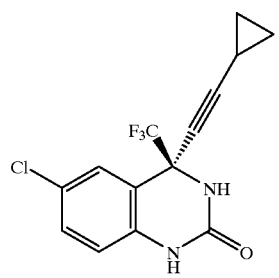
Ib comprising: contacting a quinazolinone precursor of Formula IIa or IIb:

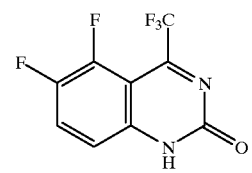
IIa

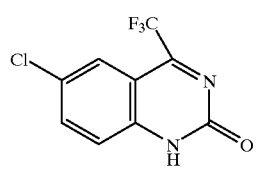
IIb with cyclopropylacetylene in the presence of a chiral moderator and a base, wherein the chiral moderator is a compound that provides an enantiomeric excess of at least 30 to 100%.

In a preferred embodiment, the chiral moderator is a compound that provides an enantiomeric excess of at least 60 to 99%.

In another preferred embodiment, the chiral moderator is a compound that provides an enantiomeric excess of at least 80 to 99%.

In another preferred embodiment, the chiral moderator is a compound that provides an enantiomeric excess of at least 85 to 99%.

In another embodiment, the contacting is performed in the presence of an additive.

In another embodiment, the additive is selected from benzene sulfonic acid, lithium trifluoromethanesulfonate (lithium triflate), lithium benzenesulfonate, 2,2,2-trifluoroethanol, (+)-camphorsulfonic acid, pyridinium p-toluenesulfonate (PPTSA), and methanesulfonic acid.

In another embodiment, the additive is benzene sulfonic acid.

In another embodiment, the stoichiometric ratios are in the range of about 0.05 to 1 equivalents of benzene sulfonic acid to 1 equivalent of quinazolinone.

In another embodiment, the stoichiometric ratios are about 0.15 equivalents of benzene sulfonic acid to 1 equivalent of quinazolinone.

In another embodiment, dehydrating is performed by heating a compound of Formula IIIa or IIIb in mesitylenes.

In another embodiment, dehydrating is performed by heating a compound of Formula IIIa or IIIb in mesitylenes in the presence of a water scavenger.

Definitions

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Suitable ether solvents include, but are not intended to be limited to, dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable hydrocarbon solvents include, but are not intended to be limited to, benzene, cyclohexane, pentane, hexane, hexanes, toluene, cycloheptane, methylcyclohexane, heptane, ethylbenzene, m-, o-, or p-xylene, mesitylene, octane, indane, nonane, or naphthalene.

Chiral moderator, as used herein, is intended to represent a compound with one or more chiral centers, preferably two chiral centers. The chiral moderator being capable of increasing the enantiomeric excess of the desired enantiomer compared with the addition reaction run without the presence of a chiral moderator.

Base, as used herein, is intended to represent a basic compound capable of deprotonating cyclopropylacetylene. Examples of such bases included, but are not intended to be limited to, n-BuLi, s-BuLi, t-BuLi, and n-HexLi, and LiHMDS.

Contacting, as used herein, is intended to represent bringing the reactants together in an appropriate medium such to allow the chemical reaction to take place.

Additives are compounds which increase the enantiomeric excess of the reaction. The additives are acids comprised of a non nucleophilic or non reactive conjugate base. Examples of such additives include, but are not intended to be limited to, benzene sulfonic acid, lithium benzenesulfonate, lithium trifluoromethanesulfonate (lithium triflate), 2,2,2-trifluoroethanol, (+)-camphorsulfonic acid, pyridinium p-toluenesulfonate (PPTSA), and methanesulfonic acid. As used herein, cyclopropylacetylene is intended to represent the use of cyclopropylacetylene in the reaction mixture. Typically, the cyclopropylacetylene is deprotonated in situ. Alternatively, cyclopropylacetylene represents the use of cyclopropylacetylide, which may be in the form of lithium cyclopropylacetylide, in the reaction mixture. The cyclopropylacetylide would be prepared prior to its addition to the reaction mixture.

Synthesis

The processes of the present invention can be practiced in a number of ways depending on the solvent, base, chiral moderator, and temperature chosen. As one of ordinary skill in the art of organic synthesis recognizes, the time for reaction to run to completion as well as yield and enantiomeric excess will be dependent upon all of the variables selected.

The following scheme shows a representation of the overall sequence of the present invention. While a specific chiral moderator is shown, this scheme is intended to be representative of the overall synthesis of compounds of Formulas Ia and Ib.

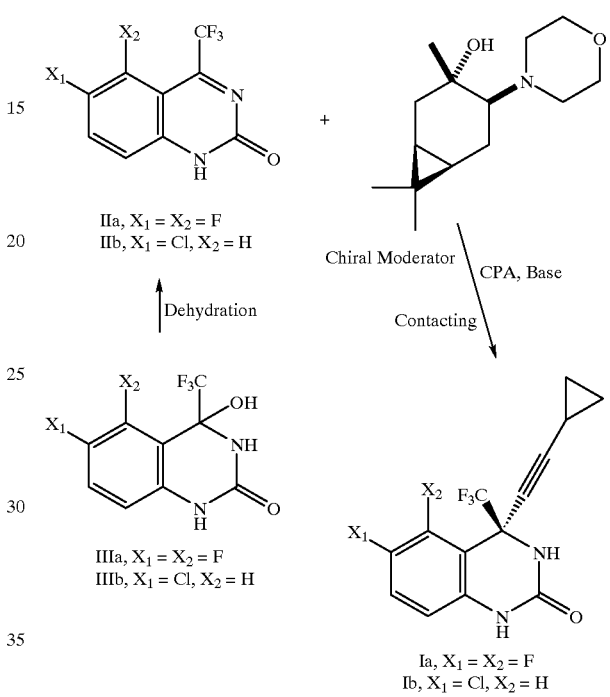

Dehydration

The quinazolinone precursor (IIa or IIb) can be prepared by known methodologies. For example, 3,4-difluoro-2-trifluoroacetyl-aniline can be reacted with potassium cyanate to yield to above precursor (IIa). The desired 6-chloro precursor can be prepared from 4-chloro-2-trifluoroacetyl-aniline.

Dehydration can be effected via a number of ways known to those of skill in the art. For example, the hydroxy group can be modified and cleaved (e.g., using acetic anhydride and a base). Another method is heating a compound of Formula IIIa or IIIb in a solvent selected from toluene and xylenes and mesitylene with or without the presence of a water scavenger. Alternatively, the dehydrating solvent is xylenes and the water scavenger is a Dean-Stark trap or a corresponding equivalent. Alternatively, the dehydrating solvent is mesitylenes with or without a water separator such as a Dean-Stark trap or a corresponding equivalent. Alternatively, the reaction is conducted in the presence of a catalyst (e.g., benzene sulfonic acid). Alternatively, o-xylene is used as the dehydration solvent. Alternatively, benzene sulfonic acid is used as the catalyst and is greater than 90% pure. Alternatively, the benzene sulfonic acid is 97% pure. In another method, the dehydrating solvent is mesitylene.

After dehydration, the resulting solution can be used directly (i.e., without purification) in the contacting step. Preferably, the solution resulting from the dehydration is reduced in volume by removal of a portion of the dehydration solvent prior to use in the contacting step.

Contacting

Enantiomeric excess (ee) is calculated by subtracting the yield of the undesired isomer from the yield of the desired isomer. For example, if the compound of Formula Ia is formed in 70% yield and its corresponding enantiomer in 30% yield, then the ee would be 40%.

A compound of Formula IIa or IIb is contacted with a chiral moderator in the presence of cyclopropylacetylene (CPA) and a base to form a compound of Formula Ia or Ib. Preferably, the chiral moderator is a compound that provides an enantiomeric excess of at least 30, 35, 40, 45, 50, 55, 60, 65, 70, 75, 80, 85, 90 95, to 100%, preferably an enantiomeric excess of at least 60, 65, 70, 75, 80, 85, 90, 95, to 99%, more preferably an enantiomeric excess of at least 80, 81, 82, 83, 84, 85, 86, 87, 88, 89, 90, 91, 92, 93, 94, 95, 96, 97, 98, to 99%, and even more preferably an enantiomeric excess of at least 85, 86, 87, 88, 90, 91, 92, 93, 94, 95, 96, 97, 98, to 99%. The reaction temperature is preferably from −20 to reflux of the solution, more preferably from −20 to room temperature. The yield of the compound of Formula Ia or Ib is preferably in excess of 50, 55, 60, 65, 70, 75, 80, 85, to 90%, more preferably in excess of 70, 75, 80, 85, to 90%.

CPA can be prepared by a number of routes known in the art. In one aspect of the invention, CPA is used as its corresponding acetylide (e.g., Li-CPA). In other words, CPA is deprotonated with a base prior to use in the contacting reaction. In this instance, a preferred acetylide is Li-CPA. Bases that can be used to deprotonate CPA include Li-HMDS (lithium hexamethyldisilazide), n-BuLi, s-BuLi, t-BuLi, and n-HexLi. In another aspect of the invention, CPA is added directly into the contacting reaction and is deprotonated in situ.

Bases that can be used for the present contacting reaction include n-BuLi, s-BuLi, t-BuLi, n-HexLi, and lithium hexamethyldisilazide (LiHMDS). The chosen base will depend upon the order in which the materials are contacted. A preferred base for the contacting reaction is LiHMDS. Another preferred base for the contacting reaction is n-HexLi. A third preferred base for the contacting reaction is n-BuLi. In another aspect of the invention, LiHMDS is prepared in situ by the addition of another lithium base to the contacting reaction having HMDS (hexamethyldisilazane) therein. The base used in the contacting reaction can serve a number of purposes. One purpose for the base is the deprotonation of the quinazolinone precursor. It should be noted that alkyl lithium bases will generally react with the quinazolinone precursors. Thus, when an alkyl lithium base is used, it should be used in a solution comprising other than the quinazolinone precursor.

The chiral moderator chosen can be one known to one of skill in the art. Chiral moderators that have been found useful (i.e., an ee of greater than 30%) include the moderators described in the embodiments. In some instances, it will be necessary for the chiral moderator to be deprotonated prior to its addition to another reactant. Alkyl lithium bases are useful for the deprotonation. Preferably n-BuLi or LiHMDS is used to deprotonate the chiral moderator. The chiral moderator can be recycled in the present reaction. For example, after contacting is complete, the chiral moderator is preferably isolated and used in another contacting reaction.

As one of ordinary skill in the art would recognize, a wide variety of stoichiometries can be selected. The stoichiometric ratios chosen will depend upon the route of addition. In general, for each equivalent of quinazolinone precursor there should be about 3 equivalents of chiral modifier, 4 equivalents of base (or bases) and at least one equivalent of cyclopropylacetylene, whether used as is or as a cyclopropylacetylide (generally at least 1.5 equivalents are used). Preferably, the stoichiometric ratios are chiral moderator 2 to 6 equivalents, cyclopropylacetylene 1 to 5 equivalents, base 4 to 8 equivalents, to quinazolinone precursor 1 equivalent. More preferably, the stoichiometric ratios are chiral moderator 3 to 4 equivalents, cyclopropylacetylene or acetylide 1 to 4 equivalents, base 4 to 7 equivalents, to quinazolinone precursor 1 equivalent. When the chiral moderator is $CM_2$, the cyclopropylacetylide is Li-CPA, the base is LiHMDS, and quinazolinone precursor is IIa, then the preferred stoichiometric ratios are 3.6:3.0:6.6:1. Alternatively, when the chiral moderator is $CM_2$, cyclopropylacetylene is used, the base is n-BuLi, HMDS is used, and the quinazolinone precursor is IIb, then the stoichiometric ratios are 3.6:1.5:6.1:1.

A variety of ways of contacting are contemplated by the present invention. A first way of contacting is by adding a quinazolinone precursor solution to a solution comprising chiral moderator, Li-CPA, and base. Preferably LiHMDS or HexLi is used as base for this route. With this method of addition, the preferred stoichiometric ratios are 2.5 to 4.5 equivalents of chiral moderator to 2.5 to 3.5 equivalents of cyclopropylacetylide to 5 to 7 equivalents of base to 1 equivalent of quinazolinone precursor. The more preferred stoichiometric ratios are 3 to 3.6 equivalents of chiral moderator to about 3 equivalents of Li-CPA to about 6.6 equivalents of LiHMDS to 1 equivalent of quinazolinone precursor.

A second way of contacting is by adding a Li-CPA, chiral moderator and base solution to a solution comprising quinazolinone precursor. Preferably LiHMDS or HexLi is used as base for this route. With this method of addition, the preferred stoichiometric ratios are 2.5 to 4.5 equivalents of chiral moderator to 2.5 to 3.5 equivalents of cyclopropylacetylide to 5 to 7 equivalents of base to 1 equivalent of quinazolinone precursor. The more preferred stoichiometric ratios are 3 to 3.6 equivalents of chiral moderator to about 3 equivalents of Li-CPA to about 6.6 equivalents of LiHMDS to 1 equivalent of quinazolinone precursor.

A third way of contacting is by adding a Li-CPA and base solution to a solution comprising chiral moderator and quinazolinone precursor. With this method of addition, the preferred stoichiometric ratios are 2.5 to 4.5 equivalents of chiral moderator to 2.5 to 3.5 equivalents of cyclopropylacetylide to 5 to 7 equivalents of base to 1 equivalent of quinazolinone precursor. The more preferred stoichiometric ratios are 3 to 3.6 equivalents of chiral moderator to about 3 equivalents of Li-CPA to about 6.6 equivalents of LiHMDS to 1 equivalent of quinazolinone precursor.

A fourth way of contacting is by adding a chiral moderator and quinazolinone precursor mixture to a solution comprising Li-CPA and base. With this method of addition, the preferred stoichiometric ratios are 2.5 to 4.5 equivalents of chiral moderator to 2.5 to 3.5 equivalents of cyclopropylacetylide to 5 to 7 equivalents of base to 1 equivalent of quinazolinone precursor. The more preferred stoichiometric ratios are 3 to 3.6 equivalents of chiral moderator to about 3 equivalents of Li-CPA to about 6.6 equivalents of LiHMDS to 1 equivalent of quinazolinone precursor.

A fifth way of contacting is by adding a Li-CPA solution to a solution comprising quinazolinone precursor IIa or IIb, chiral moderator, and base. Preferably LiHMDS is used as base for this route. With this method of addition, the preferred stoichiometric ratios are 2.5 to 4.5 equivalents of chiral moderator to 1 to 2.5 equivalents of cyclopropylacetylide to 3.5 to 5.5 equivalents of base to 1 equivalent of quinazolinone precursor. The more preferred stoichiometric ratios are 3 to 3.6 equivalents of chiral moderator to 1 to 1.5 equivalents of Li-CPA to 4 to 4.6 equivalents of LiHMDS to 1 equivalent of quinazolinone precursor.

A sixth way of contacting is by adding a solution comprising quinazolinone precursor IIa or IIb, chiral moderator, and base to a Li-CPA solution. Preferably LiHMDS is used as base for this route. With this method of addition, the preferred stoichiometric ratios are 2.5 to 4.5 equivalents of chiral moderator to 1 to 2.5 equivalents of cyclopropylacetylide to 3.5 to 5.5 equivalents of base to 1 equivalent of quinazolinone precursor. The more preferred stoichiometric ratios are 3 to 3.6 equivalents of chiral moderator to 1 to 1.5 equivalents of Li-CPA to 4 to 4.6 equivalents of LiHMDS to 1 equivalent of quinazolinone precursor.

A seventh way of contacting is adding a deprotonated chiral modifier to a solution comprising quinazolinone precursor and LiHMDS and then adding a solution comprising Li-CPA. The chiral modifier is preferably deprotonated with a second base, e.g., n-BuLi. With this method of addition, the preferred stoichiometric ratios are 2.5 to 4.5 equivalents of chiral moderator to 1 to 2.5 equivalents of cyclopropylacetylide to 1 to 1.5 equivalents of LiHMDS to 2.5 to 4.5 equivalents of second base to 1 equivalent of quinazolinone precursor. The more preferred stoichiometric ratios are 3 to 3.6 equivalents of chiral moderator to 1 to 1.5 equivalents of Li-CPA to about 1 equivalent of LiHMDS to 3 to 3.6 equivalents of n-BuLi to 1 equivalent of quinazolinone precursor.

An eighth way of contacting is by adding a quinazolinone precursor solution to a solution comprising a chiral modifier, cyclopropylacetylene, and LiHMDS and then adding a solution comprising Li-CPA. With this method of addition, the preferred stoichiometric ratios are 2.5 to 3.5 equivalents of chiral moderator to 1 to 1.5 equivalents of cyclopropylacetylene to 1 to 2.5 equivalents of Li-CPA to 3 to 5 equivalents of LiHMDS to 1 equivalent of quinazolinone precursor. The more preferred stoichiometric ratios are about 3 equivalents of chiral moderator to about 1 equivalent of cyclopropylacetylene to 1 to 1.5 equivalents of Li-CPA to about 4 equivalents of LiHMDS to 1 equivalent of quinazolinone precursor.

A ninth way of contacting is by adding a quinazolinone precursor solution to a solution containing the chiral moderator, HMDS, and n-BuLi. A cyclopropylacetylene solution is added to the reaction. With this method of addition, the preferred stoichiometric ratios are 3.6 equivalents of chiral moderator to 1.5 equivalents of cyclopropylacetylene, to 3.0 equivalents of HMDS, to 6.1 equivalents of n-BuLi, to 1 equivalent of quinazolinone presursor.

A tenth way of contacting is by adding a solution of n-butyl lithium to a solution containing the chiral moderator, HMDS, and an additive such as benzene sulfonic acid. The quinazolinone is added to the reaction followed by a cyclopropylacetylene solution. With this method of addition, the preferred stiochiometric ratios are 3.6 equivalents of chiral moderator to 1.2 equivalents of cyclopropylacetylene, to 3.0 equivalents of HMDS, to 6.1 equivalents of n-BuLi, to 1 equivalent of quinazolinone presursor.

An eleventh way of contacting is by adding to a solution chiral moderator, HMDS, a solution of n-butyl lithium, followed by the quinazolinone, benzene sulfonic acid, and then cyclopropylacetylene. With this method of addition, the preferred stiochiometric ratios are 3.6 equivalents of chiral moderator to 1.2 equivalents of cyclopropylacetylene, to 3.0 equivalents of HMDS, to 6.1 equivalents of n-BuLi, 0.15 equivalents of benzene sulfonic acid, to 1 equivalent of quinazolinone precursor.

In general, the benzene sulfonic acid is present in the range of about 0.05 to 1 equivalents to 1 equivalent of quinazolinone precursor. Alternatively, the benzene sulfonic acid is present in about 0.15 equivalents to 1 equivalent of quinazolinone precursor.

Preferably, the reaction is performed with tetrahydrofuran as a solvent. A cosolvent may also be present. The cosolvent is preferably selected from an ether or hydrocarbon. More preferably the cosolvent is selected from diethyl ether or hexanes. A quinazolinone solution can comprise quinazolinone and a solvent selected from toluene, xylenes, o-xylene, ethylbenzene, mesitylene and mixtures thereof. Preferably, a quinazolinone solution comprises quinazolinone and o-xylene, mesitylene or toluene. Alternatively, a quinazolinone solution comprises quinazolinone and o-xylene. Alternatively, a quinazolinone solution comprises quinazolinone and mestiylenes. A Li-CPA solution can comprise Li-CPA and a solvent selected from THF, methylcyclohexane (MCH), and hexanes. Preferably, a Li-CPA solution comprises Li-CPA and THF. A cyclopropylacetylene solution can comprise cyclopropylacetylene and toluene. A chiral moderator solution can comprise a chiral moderator and a solvent selected from THF, toluene, and mixtures thereof.

The following scheme describes the synthesis of 4β-morpholinocaran-3α-ol, $CM_2$.

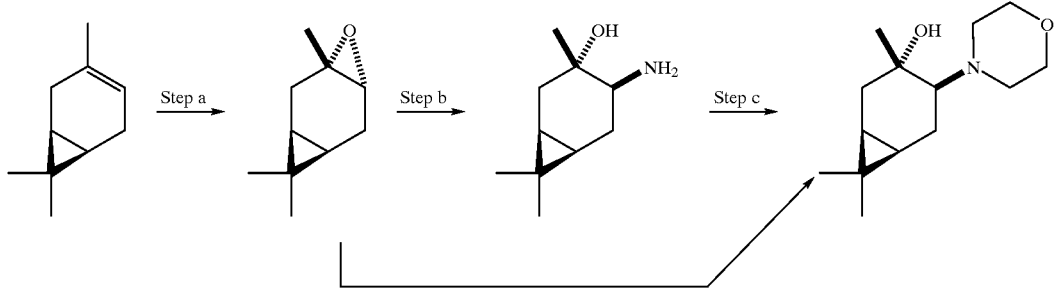

Step a
3-Carene is oxidized to its corresponding epoxide using m-CPBA in dichloromethane at room temperature in 6–8 hours.

Step b
The epoxide is opened with ammonium hydroxide, 350 psig, at 150° C. in about 24 hours.

Step c

The amino group is converted to a morpholino group by refluxing in toluene in the presence of bromoethyl ether and sodium bicarbonate to give the final product in about 20 hours.

Alternative Steps b and c

Morpholine can be used to ring open the epoxide and directly provide 4β-morpholinocaran-3α-ol. This can be done by adding morpholino to the epoxide in the presence of lithium perchlorate (see *J. Org. Chem.* 1998, 20, 7078–7082), magnesium chloride, magnesium bromide, or lithium halides.

Other features of the invention will become apparent in the course of the following descriptions of exemplary embodiments that are given for illustration of the invention and are not intended to be limiting thereof.

EXAMPLES

Example 1

Preparation of (S)-5,6-difluoro-4-(cyclopropylethynyl)-4-(trifluoromethyl)-3,4-dihydro-2(1H)-quinazolinone (Ia), Using $CM_2$ (4β-morpholinocaran-3α-ol)

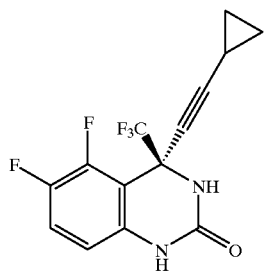

Preparation of 4β-morpholinocaran-3α-ol Solution 2,4-Dihydroxybenzoic acid salt of 4β-morpholinocaran-3α-ol (117.9 g, 0.3 M) is added to toluene (500 mL) and a solution of potassium carbonate (82.8 g, 0.61 M) in water (300 mL). The solution is stirred until the solids dissolve. The phases are separated. The organic phase is evaporated under reduced pressure to minimum volume. The residue is dissolved to a volume of 300 mL in tetrahydrofuran (THF). This solution is approximately 1 M in 4β-morpholinocaran-3α-ol.

Preparation of Lithium Cyclopropylacetylide Solution

Cyclopropylacetylene (0.15 M, 12.8 mL) is added to dry THF (80 mL) and cooled to −20° C. n-Butyl lithium (2.5 M in hexanes, 1 eq, 60.6 mL) is added while maintaining a reaction temperature of −20° C. The solution is warmed to 0° C. This solution is approximately 1 M in lithium cyclopropylacetylide.

Chiral Moderated Addition of Lithium Cyclopropylacetylide to IIa

IIa (4 g, 16 mM) is added to a solution of 4β-morpholinocaran-3α-ol (48 mM, 3 eq, 48 mL) (described above). The solution is cooled to −20° C. Lithium hexamethyldisilazide (1 M in THF, 64 mL) is added at −20° C. The solution is warmed to 60° C. and cooled to 0° C. A solution of Li-CPA in THF (1 M, 32 mL) made as described above is added. The reaction mixture is maintained at 0° C. for several hours, warmed to 20° C., and held for 16 hours.

Alternative Reaction Conditions

To a 4β-morpholinocaran-3α-ol solution (48 mM, 48 mL) is added cyclopropylacetylene (16 mM, 1.06 g, 1.4 mL). The solution is cooled to −20° C. and LiHMDS (1 M in THF, 64 mL) is added while maintaining a reaction temperature of −20° C. IIa (4 g, 16 mM) is added, the solution warmed to 60° C., and then cooled to 0° C. A solution of lithium cyclopropylacetylide (1 M, 32 mL) is added. The temperature of the reaction mixture is maintained at 0° C. for several hours, warmed to 20° C., and held for 16 hours.

Example 2

Preparation of (S)-5,6-difluoro-4-(cyclopropylethynyl)-4-(trifluoromethyl)-3,4-dihydro-2(1H)-quinazolinone (Ia), Using (1S,2R)-$CM_3$ Preparation of (1S,2R)-$CM_3$ Solution To a 300 gallon reactor is added water (165 L), (1S,2R)-$CM_3$ (75 kg) and methylcyclohexane (MCH, 289 kg). 30% NaOH (aq.) solution (41.8 kg) is added while maintaining a temperature of less than 30° C. The pH of the aqueous solution phase is assayed to ensure it is >13 and the mixture is warmed to 30° C. The phases are separated and the organic layer is washed with 188 L of water. The organic solution is concentrated by distillation to about 230 L and cooled to 20° C.

Preparation of IIa

IIIa is added to a 300 gallon reactor followed by benzene sulphonic acid (250 g) and xylenes (215 kg). The slurry is heated to reflux and the distillate is cycled through a Dean Stark trap to collect the water generated during the dehydration process. Heating is continued until about 1.6 L of water is collected and the solution is then cooled to 60° C. After a greater than 96% conversion is observed, the solution is concentrated to about 2.0 L/kg of xylenes relative to IIa and the resultant slurry is cooled to 20° C.

Preparation of Ia

To a 200 gallon reactor is charged the (1S,2R)-$CM_3$ solution (259 kg containing about 2.5 eq. of $CM_3$ or 15.9 kg). The solution is concentrated by vacuum distillation to a minimum volume (about 45 L) and THF (178 L) is added. The solution is cooled to −15° C. and n-hexyllithium solution (174.3 kg, 24 wt. % in hexanes, 4.95 eq.) is added while maintaining a temperature of less than 0° C. The solution is cooled back to −15° C. and lithium cyclopropylacetylide (16.6 kg, 2.5 eq.) is added. The resultant solution is held at 20 to 25° C. for 1 h.

The lithium cyclopropylacetylide solution is added to the IIa/xylenes slurry and the resulting red/brown solution is maintained at 25° C. and held for 12 to 16 h. Conversion of IIa to Ia is assayed and if not greater than 99%, the reaction mixture is heated to 50 to 60° C. and held until greater than 99% conversion is obtained. After greater than 99% conversion is obtained, the solution is cooled to 10° C. and 2.5 N HCl (162 kg, 7.0 eq) aqueous solution is added while maintaining the temperature below 35° C. The pH of the mixture is checked to see if it is <4 and adjusted with 37% HCl (aq.) if it is not <4. The mixture is agitated to promote crystallization of the racemate and is held until the mother liquor enantiomeric purity is >98% Ia. The three phase mixture is filtered to remove the racemate-solvate and the resultant two phase mixture is then allowed to separate. The aqueous acid stream is retained for recycling of the chiral moderator and the organic solution is washed with 10% $KHCO_3$ (5 L/kg of IIa) and water (125 L). The organic solution is concentrated by vacuum distillation to about 380 L (20 L/kg) and the solution filtered for clarification. The vacuum distillation is continued until a final volume of about 50 L is achieved (about 2.5 L/kg). The solution is sampled and assayed to ensure removal of THF (<1.0% v/v). The solution is warmed to 60 to 65° C. and maintained as heptane (121 kg) is added. The solution is cooled to 0° C. over 4 h and the mother liquor concentration is determined by HPLC with the object of having <1.0 wt. % of Ia. The product is isolated by centrifugation and the wet cake is washed with heptane (25 kg). The product is dried at 95° C. under vacuum to a constant weight. 15.0 Kg of Ia is obtained (50%).

Example 3

Preparation of (S)-6-chloro-4-(cyclopropylethynyl)-4-(trifluoromethyl)-3,4-dihydro-2(1H)-quinazolinone (Ib)

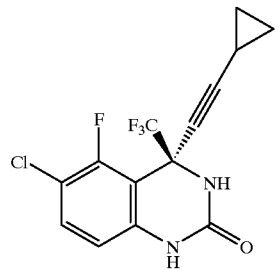

The compound Ib can be prepared similarly to Ia, except that IIb instead of IIa is used as the starting material.

Example 4

Preparation of (S)-6-chloro-4-(cyclopropylethynyl)-4-(trifluoromethyl)-3,4-dihydro-2(1H)-quinazolinone (Ib)

4β-Morpholinocaran-3α-ol ($CM_2$) (43.0 g, 0.18 mol) dissolved in 50 mL of toluene was slurried with IIb (12.4 g, 0.050 mol). The mixture was cooled to −5° C. and a 1M solution of LiHMDS in THF (250 mL, 0.250 mol) was added at a rate that the pot temperature was kept under 10° C. The mixture was then heated to 70° C., maintained for 1 hour, and cooled to −15° C. Li-CPA was prepared in a separate pot by dissolving cyclopropylacetylene (6.6 g, 0.100 mol) in THF (25 mL) and adding 2.5M butyllithium (40 mL, 0.100 mol). The Li-CPA slurry was slowly added to the $CM_2$/IIb mixture. The mixture was allowed to reach room temperature over a period of 18 hours. The reaction was complete and the chiral purity was 97.7:2.3 (S:R enantiomeric ratio). The mixture was quenched with 2M aqueous citric until the pH of the aqueous layer was 3. Layers were separated. The organic layer was washed with water, then it was concentrated and heptane (100 mL) was added. Ib crystallized as a white solid. The slurry was filtered, washed with heptane (30 mL), and dried to constant weight to yield 12.8 g of Ib (81.5%) with a chiral purity of 99.2% (S enantiomer).

Example 5

Preparation of (S)-6-chloro-4-(cyclopropylethynyl)-4-(trifluoromethyl)-3,4-dihydro-2(1H)-quinazolinone (Ib)

4β-Morpholinocaran-3α-ol (40.3 g, 0.17 mol) and IIb (12.4 g, 0.050 mol) were slurried in THF (45 mL). The mixture was cooled to −5° C. A LiHMDS slurry in THF was prepared by adding 10M BuLi (22 mL, 0.22 mol) to a solution of HMDS (1,1,1,3,3,3-hexamethyldisilazane, 36.2 g, 0.22 mol) in THF (40 mL) and it was added to the $CM_2$/IIb mixture at a rate that the pot temperature was kept under 10° C. The mixture was then heated to 60° C., maintained for 1 hour, and cooled to −15° C. Li-CPA was prepared in a separate pot by dissolving cyclopropylacetylene (5.9 g, 0.090 mol) in THF (30 mL) and adding 10M butyllithium (7.5 mL, 0.075 mol). The Li-CPA solution at −15° C. was slowly added to the $CM_2$/IIb mixture. The mixture was allowed to reach room temperature over a period of 16 hours. The conversion was 86%, so 1M LiHMDS (5 mL, 0.005 mol) was added. It was stirred at room temperature and conversion was >97%, and the chiral purity was 98.4:1.6 (S:R enantiomeric ratio). The mixture was cooled to −10° C. and quenched with water (100 mL). Layers were allowed to separate. The organic layer was diluted with toluene (50 mL) and washed with water (50 mL), then with 2M citric acid until pH=3, and then with water. The resulting organic layer was concentrated to 75 grams and solvent exchanged with heptane until chiral HPLC of the mother liquor showed an enantiomeric ratio of 56:44 (S:R). The slurry was filtered, the cake was washed with heptane (50 mL) and it was dried until constant weight in vacuum oven at 60° C. to yield 13.4 g of Ib (85% yield), with a chiral purity of 99.6% (S enantiomer).

Example 6

Preparation of (S)-6-chloro-4-(cyclopropylethynyl)-4-(trifluoromethyl)-3,4-dihydro-2(1H)-quinazolinone (Ib)

4β-Morpholinocaran-3α-ol-toluene solution (129.0 g (159.0 g of solution) 0.540 mol) was diluted with 150 mL of THF. It was cooled to −25° C. and n-BuLi (2.5 M, 270 mL, 0.68 mol) was slowly added. Then HMDS (23.7 g, 0.15 mol) was added, the mixture was heated to 30° C. and 170 mL of solvent was distilled out. The solution was cooled to 6° C. and IIb (37.2 g, 0.150 mol) slurried in 90 mL of THF was added. The mixture was heated to 40–50° C. for 1 h, then it was cooled to −20° C. Li-CPA was prepared by dissolving CPA (16.5 g, 0.25 mol) in THF (90 mL) and adding n-BuLi (2.5 M, 90 mL, 0.225 mol). The Li-CPA slurry was cooled and added to the $CM_2$/IIb mixture. It was allowed to reach room temperature overnight. Additional Li-CPA was added (0.12 mol) to accelerate the reaction, which completed within 10 hours. The chiral purity of the Ib formed was 95.3%. The mixture was cooled to 5° C. and quenched with 250 mL of water. After filtration through Dacron™ to eliminate a small amount of solid from the interface, layers were separated. The organic layer was diluted with toluene (100 mL) and washed with 100 mL of water, then it was extracted with citric acid (2M) until pH=3. The organic layer was then washed with $KHCO_3$ and with water until pH=6–7. The organic layer was solvent exchanged with heptane. Ib crystallized as an off white solid, which was filtered and washed with heptane, and dried until constant weight in a vacuum oven at 70° C. to yield 37.1 g (79%) with a chiral purity of 99.4%.

Example 7

Preparation of (S)-6-chloro-4-(cyclopropylethynyl)-4-(trifluoromethyl)-3,4-dihydro-2(1H)-quinazolinone (Ib)

4β-Morpholinocaran-3α-ol (4.3 g, 0.018 mol) was slurried in THF (5 mL) and cooled to −5° C. Butyllithium (2.5M, 9.2 mL, 0.023 mol) was slowly added, then CPA (0.66 g, 0.010 mol) and LiHMDS/THF (1M, 10 mL, 0.010 mol). The mixture was heated to 60–70° C. and maintained for 1 hour, then it was cooled to −10° C. A slurry of IIb in 5 mL of THF was then added, and the mixture was allowed to reach room temperature overnight. Conversion was 98% and chiral purity was 96%. The reaction mixture was quenched with 1M citric acid, then the organic layer was washed with water, concentrated and solvent exchanged with heptane. Ib crystallized as an off white solid, which was filtered and washed with heptane to yield 75%. It was enriched in the S enantiomer with a chiral purity of 99.6%.

Example 8

Preparation of (S)-6-chloro-4-(cyclopropylethynyl)-4-(trifluoromethyl)-3,4-dihydro-2(1H)-quinazolinone (Ib)

4β-Morpholinocaran-3α-ol (4.3 g, 0.018 mol) was dissolved in THF (5 mL) and 1M LiHMDS/THF solution (28.5 mL, 0.0285 mol) and CPA (0.40 g, 0.0061 mol) was then added. The mixture was heated to reflux (69° C.) and held for 1 hour. Then it was cooled to −12° C. In a separate pot IIb (1.24 g, 0.005 mol) was slurried in THF (5 mL). This slurry was added to the CM$_2$/CPA mixture. Then it was allowed to warm to room temperature. After 18 h, conversion was 94%, and after 48 hours, the conversion was 97.6%, with a chiral purity of 95.8%. The mixture was quenched with 1M citric acid and washed with water. The organic layer was concentrated to a paste.

Example 9

Preparation of (S)-6-chloro-4-(cyclopropylethynyl)-4-(trifluoromethyl)-3,4-dihydro-2(1H)-quinazolinone (Ib)

4β-Morpholinocaran-3α-ol (500 mg, 6.0 eq.) and CPA (69 mg, 3.0 eq) are dissolved in a dry flask with THF (3 mL) and the solution is cooled to −50 C. The 1M LiHMDS (3.1M, 9.0 eq.) is added and the reaction is aged briefly at 0° C. before being held at −20 for 1 hour. IIb (87 mg, 1.0 eq.) is then added to the pot as a solid. The reaction is then held at 0° C. (6 hr) before warming to rt overnight. The reaction gives 90% conversion and 96% ee.

Example 10

Preparation of (S)-6-chloro-4-(cyclopropylethynyl)-4-(trifluoromethyl)-3,4-dihydro-2(1H)-quinazolinone (Ib)

Following the identical conditions of Example 9, except that CM$_1$ instead of CM$_2$ is used, provides Ib. The reaction gives 90% conversion and 87% ee.

Example 11

Preparation of (S)-5,6-difluoro-4-(cyclopropylethynyl)-4-(trifluoromethyl)-3,4-dihydro-2(1H)-quinazolinone (Ia)

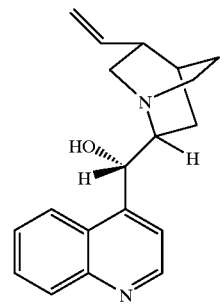

The above chiral moderator (1.34 g, 3.0 eq.) and CPA (4.0 eq) are dissolved in a dry flask with THF (40 mL) and the solution is cooled to −50° C. The 2.5M n-BuLi (4.22 mL, 7.0 eq.) is added and the reaction is aged briefly at 0° C. before being held at −50° C. for 1 hour. IIa is then added to the pot as a solid. The reaction is then held at −20° C. (2 hr). The reaction gives 100% conversion of starting material and 85% e.e., but results in largely the precursor being reduced (90%).

Example 12

Preparation of (S)-5,6-difluoro-4-(cyclopropylethynyl)-4-(trifluoromethyl)-3,4-dihydro-2(1H)-quinazolinone (Ia)

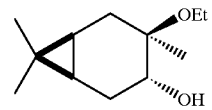

The above chiral moderator (200 mg, 6.0 eq) and CPA (33.4 mg, 3.0 eq) are dissolved in a dry flask with THF and the solution is cooled to −50° C. Then, 1.0M LiHMDS (1.51 mL, 9.0 eq) is added and the reaction is aged briefly at 0° C. before being held at −20° C. for 1 hour. Ketimine IIa (50 mg, 1.0 eq) is then added to the pot as a solid. The reaction is then held at 0° C. (6 hr) before warming to room temperature overnight. The reaction gives 90% conversion and 88% ee.

Example 13

Preparation of the Lithium Salt of IIb

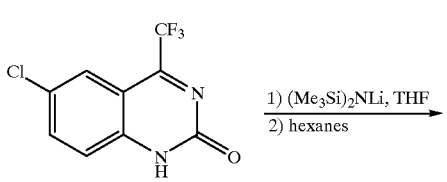

-continued

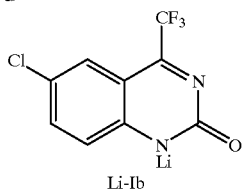

Li-Ib

To a 500 mL round-bottom flask equipped with a Teflon®-coated stir bar was charged anhydrous THF (15 mL) and hexamethyldisilazane (3.89 g, 0.024 mol). The stirred solution was cooled to 0° C., and n-butyllithium (9.65 mL of a 2.5 M solution in hexanes, 0.024 mol) was added via syringe at a rate such that the internal temperature was maintained at or below 10° C. After addition was complete, the solution was again cooled to 0° C. and subsequently treated with IIb (6.00 g, 0.024 mol). The resulting mixture was warmed to 21° C. over 1 hour to give a clear, amber-colored solution. Addition of anhydrous hexanes (300 mL) induced precipitation of a voluminous yellow solid that was isolated by vacuum filtration and dried at 80° C. under vacuum for approximately 50 hours to give a fine yellow powder (5.20 g, 85.1% yield).

Example 14

Preparation of the Lithium Salt of $CM_2$

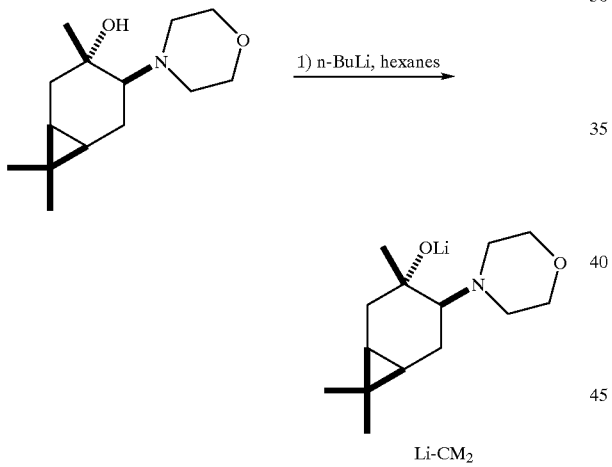

To a 100 mL round-bottom flask equipped with a Teflon®-coated stir bar was charged anhydrous hexanes (20 mL) and $CM_2$ (4.32 g, 0.018 mol). The stirred solution was cooled to −25° C. and then treated with n-butyllithium (7.22 mL of a 2.5 M solution in hexanes, 0.018 mol). The resulting mixture was warmed to 20° C. over 30 minutes to give a clear, light yellow solution. Concentration in vacuo yielded a foamy white solid (4.64 g, quantitative yield) that did contain some traces of residual solvent, as determined by $^1$H-NMR spectroscopy.

Example 15

Preparation of (S)-6-chloro-4-(cyclopropylethynyl)-4-(trifluoromethyl)-3,4-dihydro-2(1H)-quinazolinone (Ib)

To a 100 mL three-neck round-bottom flask equipped with a Teflon®-coated stir bar was charged anhydrous THF (5 mL), triphenylmethane (0.02 g, 0.08 mmol), and $CM_2$ (4.32 g of a 50% (wt/wt) solution in toluene, 9.02 mmol). With stirring, the reaction was cooled to −25° C. and treated with n-butyllithium (3.61 mL of a 2.5 M solution in hexanes, 9.02 mmol) to give a clear, light-pink solution. The reaction was then warmed to 0° C. and treated with a slurry of the lithium salt of IIb (0.64 g, 2.51 mmol) in 5 mL of anhydrous THF to give a clear, light yellow solution. The resulting mixture was stirred at 60° C. for 1 hour, thus yielding a clear, amber colored solution that was subsequently cooled to −20° C. and treated with a solution of lithium cyclopropylacetylide (0.36 g in 5 mL anhydrous THF, 5.00 mmol). The reaction was held at −10° C. for 1 hour, and then warmed to 21° C. and stirred for approximately 13 hours. HPLC analysis showed a solution yield of Ib in excess of 90%, with a 96.6/3.4 ratio of enantiomers (in favor of the desired stereoisomer).

Example 16

Preparation of (S)-6-chloro-4-(cyclopropylethynyl)-4-(trifluoromethyl)-3,4-dihydro-2(1H)-quinazolinone (Ib)

To a 100 mL three-neck round-bottom flask equipped with a Teflon®-coated stir bar was charged anhydrous THF (10 mL), triphenylmethane (0.02 g, 0.08 mmol), and $CM_2$ (4.32 g, 18.0 mmol). With stirring, the reaction was cooled to −25° C. and treated with n-butyllithium (1.80 mL of a 10.0 M solution in hexanes, 18.0 mmol) to give a clear, light-pink solution. The reaction was then warmed to 0° C. and treated with a slurry of the lithium salt of IIb (1.28 g, 5.02 mmol) in 4 mL of anhydrous THF to give a clear, light yellow solution. The resulting mixture was stirred at 60° C. for 1 hour, thus yielding a clear, amber colored solution that was subsequently cooled to −20° C. and treated with a slurry of lithium cyclopropylacetylide (0.72 g in 9 mL anhydrous THF, 10.0 mmol). The reaction was held at −10° C. for 1 hour, and then warmed to 21° C. and stirred for approximately 13 hours. HPLC analysis showed a solution yield of Ib in excess of 90%, with a 95.4/3.6 ratio of enantiomers (in favor of the desired stereoisomer).

Example 17

Preparation of (S)-6-chloro-4-(cyclopropylethynyl)-4-(trifluoromethyl)-3,4-dihydro-2(1H)-quinazolinone (Ib)

To a 100 mL three-neck round-bottom flask equipped with a Teflon®-coated stir bar was charged anhydrous THF (15 mL), the lithium salt of $CM_2$ (4.64 g of material that is 93% pure (estimated by $^1$H-NMR, contaminated with hexanes), 18.0 mmol), and a slurry of the lithium salt of IIb (1.28 g, 5.02 mmol) in 5 mL of anhydrous THF to give a chalky yellow suspension. The resulting mixture was stirred at 60° C. for 1 hour, thus yielding a clear, amber colored solution that was subsequently cooled to −18° C. and treated with a solution of lithium cyclopropylacetylide (0.72 g in 10 mL anhydrous THF, 10.0 mmol). The reaction was held at −10° C. for 1 hour, and then warmed to 20° C. and stirred for approximately 5 hours. HPLC analysis showed a solution yield of Ib in excess of 90 %, with a 94.9/5.1 ratio of enantiomers (in favor of the desired stereoisomer).

Example 18

Preparation of (S)-6-chloro-4-(cyclopropylethynyl)-4-(trifluoromethyl)-3,4-dihydro-2(1H)-quinazolinone (Ib)

A 2000 mL 4-neck round-bottomed flask, equipped with an overhead stirring device, a water-cooled reflux condenser, and a PTFE-coated thermocouple was charged with a solution of $CM_2$ (252.53 g of a solution comprising 54.9% (wt/wt) $CM_2$, 18.4% (wt/wt) toluene, and the balance THF, 0.579 mol, 3.6 eq), 1,1,1,3,3,3-hexamethyldisilazane (133.86 g, 0.804 mol, 5.0 eq), and 118 mL anhydrous THF. The resulting solution was cooled to ca. −10° C. and then n-butyllithium (94.38 mL of a 10.4 M solution in hexanes, 0.982 mol, 6.1 eq) was added via addition funnel, in a dropwise manner, at a rate such that the reaction temperature did not exceed 10° C. After 15 minutes of stirring at 20–25° C. under vacuum (typically 100–150 mbar, thus effecting vacuum distillation of n-butane), the resulting light orange-colored solution was cooled to 0° C., and to it was added IIb (40.0 g, 0.161 mol, 1.0 eq) via glass funnel, chased with 10 mL of anhydrous THF. The resulting slurry was warmed to 30° C. and stirred at that temperature for 2 hours to effect aging. The reaction was then cooled to ca. −15° C. and then treated with cyclopropylacetylene (18.2 g of a 70% (wt/wt) solution in toluene, 0.193 mol, 1.2 eq). Once the addition was complete, the reaction was placed in an ice-water bath, thus warming it to ca. 0° C., where it was held for approximately 8 hours. The reaction was then treated with an additional charge of cyclopropylacetylene (4.6 g of a 70 % (wt/wt) solution in toluene, 0.048 mol, 0.3 eq), warmed to 30° C. and held for 2 hours, at which time HPLC analysis confirmed complete consumption of IIb. HPLC analysis showed a solution yield of Ib in excess of 95%, with a 96.6/3.4 ratio of enantiomers (in favor of the desired stereoisomer).

Example 19

Preparation of (S)-6-chloro-4-(cyclopropylethynyl)-4-(trifluoromethyl)-3,4-dihydro-2(1H)-quinazolinone (Ib)

To a 50 gallon glass-lined reactor was charged 63.4 kg of a 55% (wt/wt) solution of $CM_2$ in toluene/THF (3.6 eq IK893), 28.4 kg tetrahydrofuran and 20.1 kg 1,1,1,3,3,3-hexamethyldisilazane (3.0 eq), and the system was thoroughly purged with dry nitrogen. KF titration of the resulting solution showed a water content of 249.4 ppm (spec≦500 ppm). The reactor was vented to a thermal oxidizer and the contents were cooled to −15 ° C. with stirring at 100 RPM. The cooled solution was then treated with 17.1 kg of 10.0 M n-butyllithium in hexanes (6.1 eq n-BuLi), maintaining the temperature ≦5° C., and the transfer lines were chased with 1.0 kg heptanes—the addition required approximately 4 hours. The resulting mixture was then warmed to 10° C. and the reactor pressure was decreased to 300 mm Hg over 1 hour, and then held at 300 mm Hg for 10 minutes, thus effecting vacuum distillation of n-butane (which was subsequently discharged to the thermal oxidizer). The reaction was again cooled to −15° C., treated with 10.0 kg of IIb (1.0 eq), and then warmed to 30° C. and held for two hours to effect aging. Next, the reaction was cooled to between −10 and −15° C. and treated with 4.6 kg of a 70% (wt/wt) cyclopropylacetylene solution in toluene (1.2 eq CPA) while maintaining the reaction temperature ≦−5° C. The transfer line was chased with 1.0 kg THF, and the reaction was warmed to −2° C. and held for 11 hours to give 83.2% conversion with a 97.7/2.3 ratio of enantiomers (in favor of the desired stereoisomer). The reaction was then treated with an additional 1.1 kg of cyclopropylacetylene solution (0.3 eq CPA) and warmed to 30° C. pending a 2 hour hold at 5° C. After 6 hours at 30° C. the reaction reached 98.03% conversion with a 97.5/2.5 ratio of enantiomers (in favor of the desired stereoisomer).

Example 20

Preparation of (S)-6-chloro-4-(cyclopropylethynyl)-4-(trifluoromethyl)-3,4-dihydro-2(1H)-quinazolinone (Ib)

Preparation of IIb

To a 1600 L glass-lined reactor was charged IIIb (85.0 kg, 318.8 mol, 1.0 eq) and mesitylene (734 kg, 850 L). The resulting slurry was heated to reflux (152–167° C.) over two hours, held at reflux for 90 minutes, and subsequently concentrated to ca. 510 L. Upon completion, the reaction was cooled to 20° C. and held for 1 hour. The resulting slurry was discharged to a centrifuge and the resulting wetcake was washed twice with 151.5 kg of heptane. The solid was dried in a tumble drier (90–100° C., 5 RPM, full house vacuum) until the residual IIIb level was <0.5% (determined by differential scanning calorimetry), thus providing 75.0 kg of IIb (94.6% yield).

Preparation of Ib

A 3.0 L 4-neck round-bottomed flask, equipped with an overhead stirring device, a water-cooled reflux condenser, and a PTFE-coated thermocouple was charged with a solution of $CM_2$ (845.4 g of a 61.5% (wt/wt) $CM_2$ solution, 2.17 mol, 3.6 eq), 1,1,1,3,3,3-hexamethyldisilazane (301.2 g of a 97% (wt/wt) solution (Dow Corning), 1.81 mol, 3.0 eq), and 480 mL anhydrous THF. The resulting solution was cooled to ca. −10° C. and then n-butyllithium (368.1 mL of a 10.0 M solution in hexanes, 3.68 mol, 6.1 eq) was added via addition funnel at a rate such that the reaction temperature did not exceed 20° C. After 15 minutes of stirring at 20–25° C. under vacuum (typically 100–150 mbar, thus effecting vacuum distillation of n-butane), the resulting light orange-colored solution was cooled to 0° C., and to it was added IIb (150.0 g, 0.60 mol, 1.0 eq) via glass funnel, followed by benzenesulfonic acid (14.32 g of Fluka 98% pure, anhydrous material, 0.09 mol, 0.15 eq) and chased with 20 mL of anhydrous THF. The resulting slurry was warmed to 30° C. and stirred at that temperature for 2 hours to effect aging, thus providing an amber-colored solution. The reaction was then cooled to ca. −10° C. and then treated with cyclopropylacetylene (68.4 g of a 70% (wt/wt) solution in toluene, 0.72 mol, 1.2 eq). Once the addition was complete, the reaction was placed in an ice-water bath, thus warming it to ca. 0° C., where it was held for approximately 3 hours. At the conclusion of the 3 hour hold, HPLC analysis revealed that reaction conversion was 78%, and the solution e.p. was 98.7%. The reaction was then removed from the cooling bath and warmed to room temperature at a rate of approximately 12° C. per hour. After approximately 1 hour ($T_{internal}$=12° C.), reaction conversion was 83% and solution e.p. was unchanged at 98.7%. The reaction was left stirring under dry nitrogen overnight (ca. 13 hours), and the following morning HPLC analysis indicated the reaction conversion to be 99.0%, again with a solution e.e of 97.4%.

Obviously, numerous modifications and variations of the present invention are possible in light of the above teachings. It is therefore to be understood that within the scope of the appended claims, the invention may be practiced otherwise than as specifically described herein.

What is claimed is:
1. A process for making a compound of Formula Ia or Formula Ib:
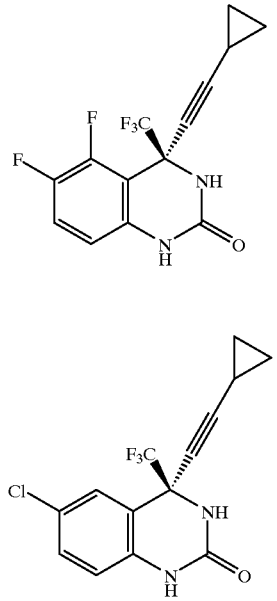
comprising: contacting a quinazolinone precursor of Formula IIa or IIb:
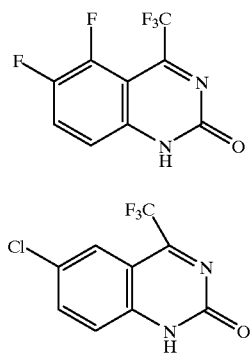
with cyclopropylacetylene in the presence of a chiral moderator and a base, wherein the chiral moderator is a compound selected from:
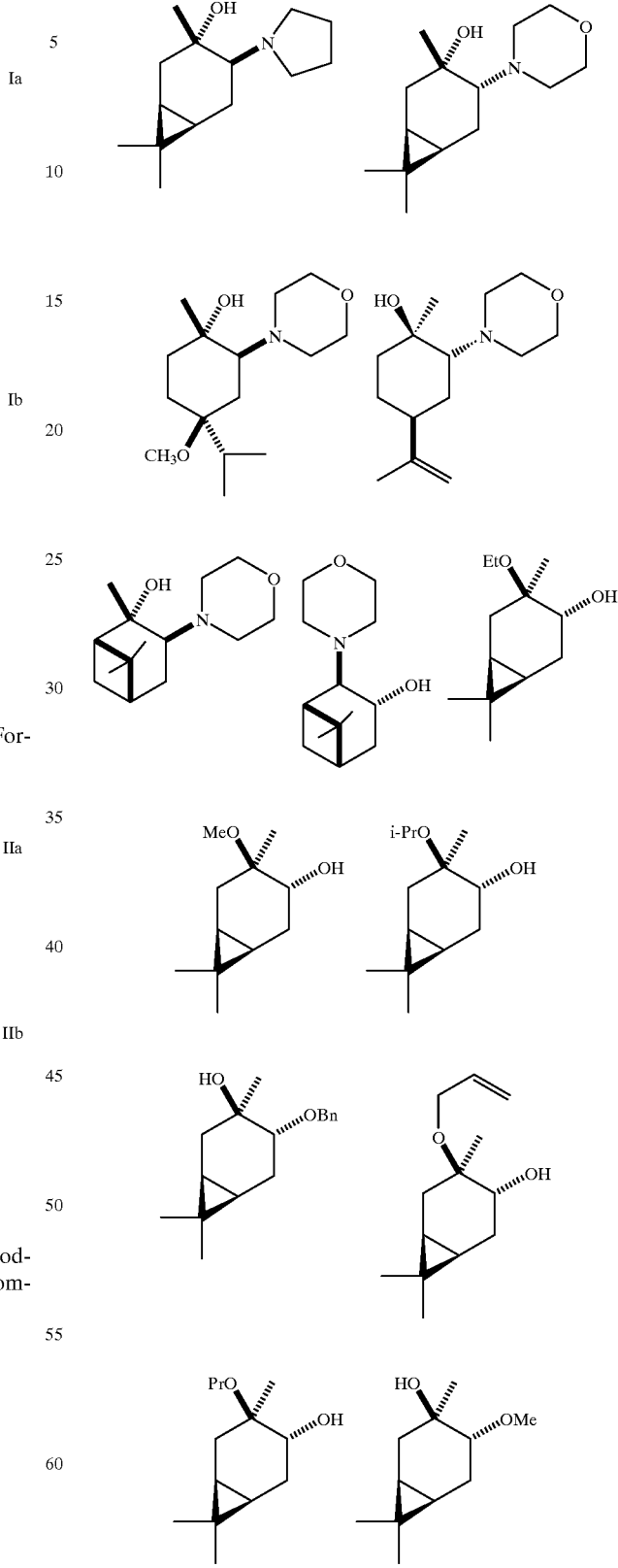

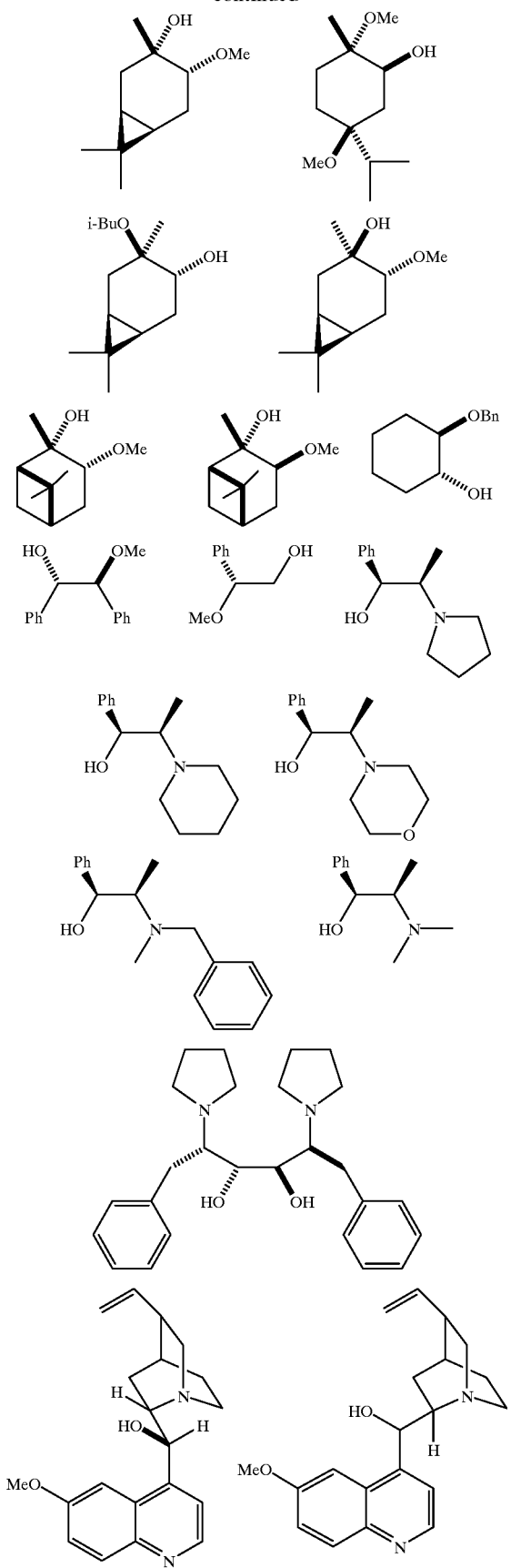
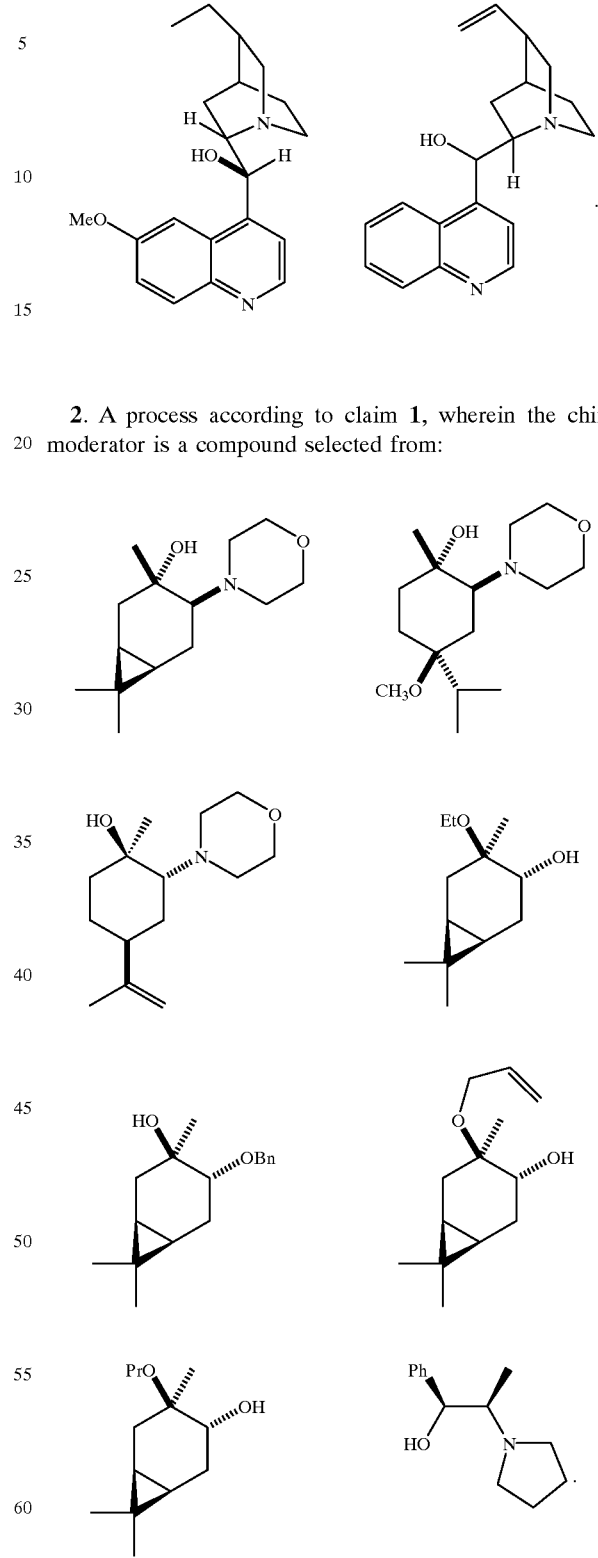
2. A process according to claim 1, wherein the chiral moderator is a compound selected from:
3. A process according to claim 1, wherein the chiral moderator (CM) is selected from:

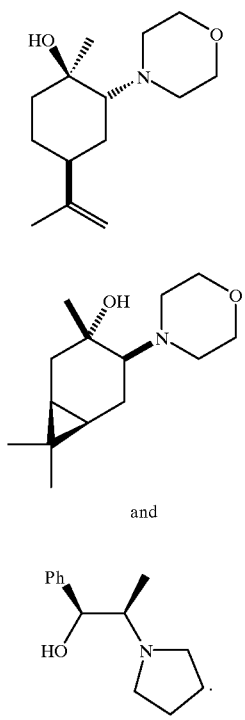

4. A process according to claim 3, wherein the chiral moderator is CM₁.

5. A process according to claim 3, wherein the chiral moderator is CM₂.

6. A process according to claim 3, wherein the chiral moderator is CM₃.

7. A process according to claim 1, wherein the cyclopropylacetylene is lithium cyclopropylacetylide.

8. A process according to claim 1, wherein the contacting is performed with tetrahydrofuran as a solvent.

9. A process according to claim 1, wherein the base is selected from lithium hexamethyldisilazide, n-BuLi, s-BuLi, t-BuLi, and n-HexLi.

10. A process according to claim 9, wherein the base is n-HexLi or n-BuLi.

11. A process according to claim 9, wherein the base is lithium hexamethyldisilazide.

12. A process according to claim 1, wherein contacting is performed with tetrahydrofuran as a solvent and lithium hexamethyldisilazide as a base.

13. A process according to claim 1, wherein contacting is performed by adding a solution, comprising: a quinazolinone precursor to a solution comprising chiral moderator, Li-CPA, and base.

14. A process according to claim 13, wherein the stoichiometric ratios are 3 to 3.6 equivalents of chiral moderator to about 3 equivalents of Li-CPA to about 6.6 equivalents of LiHMDS to 1 equivalent of quinazolinone precursor.

15. A process according to claim 1, wherein contacting is performed by adding a solution, comprising: Li-CPA, chiral moderator and base to a solution comprising quinazolinone precursor.

16. A process according to claim 15, wherein the stoichiometric ratios are 3 to 3.6 equivalents of chiral moderator to about 3 equivalents of Li-CPA to about 6.6 equivalents of LiHMDS to 1 equivalent of quinazolinone precursor.

17. A process according to claim 1, wherein contacting is performed by adding a solution, comprising: Li-CPA and base to a solution comprising chiral moderator and quinazolinone precursor.

18. A process according to claim 17, wherein the stoichiometric ratios are 3 to 3.6 equivalents of chiral moderator to about 3 equivalents of Li-CPA to about 6.6 equivalents of LiHMDS to 1 equivalent of quinazolinone precursor.

19. A process according to claim 1, wherein contacting is performed by adding a solution, comprising: chiral moderator and quinazolinone precursor to a solution comprising Li-CPA and base.

20. A process according to claim 19, wherein the stoichiometric ratios are 3 to 3.6 equivalents of chiral moderator to about 3 equivalents of Li-CPA to about 6.6 equivalents of LiHMDS to 1 equivalent of quinazolinone precursor.

21. A process according to claim 1, wherein contacting is performed by adding a solution, comprising: Li-CPA to a solution comprising quinazolinone precursor IIa or IIb, chiral moderator, and base.

22. A process according to claim 21, wherein the stoichiometric ratios are 3 to 3.6 equivalents of chiral moderator to 1 to 1.5 equivalents of Li-CPA to 4 to 4.6 equivalents of LiHMDS to 1 equivalent of quinazolinone precursor.

23. A process according to claim 1, wherein contacting is performed by adding a solution comprising quinazolinone precursor IIa or IIb, chiral moderator, and base to a solution, comprising: Li-CPA.

24. A process according to claim 23, wherein the stoichiometric ratios are 3 to 3.6 equivalents of chiral moderator to 1 to 1.5 equivalents of Li-CPA to 4 to 4.6 equivalents of LiHMDS to 1 equivalent of quinazolinone precursor.

25. A process according to claim 1, wherein contacting is performed by adding a solution, comprising: deprotonated chiral modifier to a solution, comprising: quinazolinone precursor and LiHMDS and then adding a solution, comprising: Li-CPA.

26. A process according to claim 25, wherein the stoichiometric ratios are 3 to 3.6 equivalents of chiral moderator to 1 to 1.5 equivalents of Li-CPA to about 1 equivalent of LiHMDS to 3 to 3.6 equivalents of n-BuLi to 1 equivalent of quinazolinone precursor.

27. A process according to claim 1, wherein contacting is performed by adding a solution, comprising: quinazolinone precursor to a solution, comprising: a chiral modifier, cyclopropylacetylene, and LiHMDS and then adding a solution, comprising: Li-CPA.

28. A process according to claim 27, wherein the stoichiometric ratios are about 3 equivalents of chiral moderator to about 1 equivalent of cyclopropylacetylene to 1 to 1.5 equivalents of Li-CPA to about 4 equivalents of LiHMDS to 1 equivalent of quinazolinone precursor.

29. A process according to claim 1, wherein the quinazolinone precursor of Formula IIa or IIb:

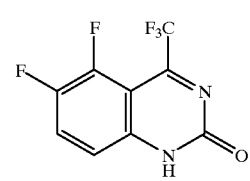

IIa

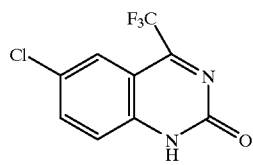

is prepared by the process, comprising: dehydrating a compound of Formula IIIa or IIIb:

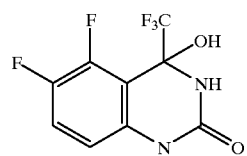

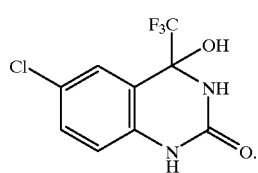

30. A process according to claim 29, wherein dehydrating is performed by heating a compound of Formula IIIa or IIIb in a solvent selected from toluene, xylenes, and mesitylenes in the presence of a water scavenger.

31. A process according to claim 30, wherein the dehydrating solvent is xylenes, the water scavenger is a Dean-Stark trap, and the reaction is conducted in the presence of benzene sulfonic acid.

32. A process according to claim 31, wherein the reaction solution resulting from dehydration is reduced in volume and used in the contacting reaction without further purification.

33. A process for making a compound of Formula Ia or Formula Ib:

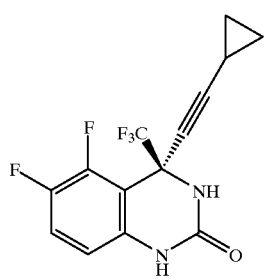

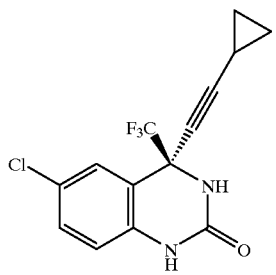

comprising: contacting a quinazolinone precursor of Formula IIa or IIb:

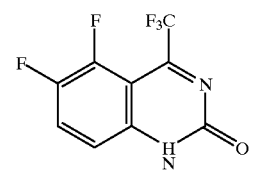

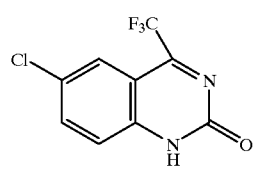

with cyclopropylacetylene in the presence of a chiral moderator and a base, wherein the chiral moderator is a compound that provides an enantiomeric excess of at least 30 to 100%.

34. A process according to claim 33, wherein the chiral moderator is a compound that provides an enantiomeric excess of at least 60 to 99%.

35. A process according to claim 34, wherein the chiral moderator is a compound that provides an enantiomeric excess of at least 80 to 99%.

36. A process according to claim 35, wherein the chiral moderator is a compound that provides an enantiomeric excess of at least 85 to 99%.

37. A process according to claim 1, wherein contacting is performed by adding a solution, comprising: quinazolinone precursor to a solution, comprising: a chiral modifier, HMDS, and n-BuLi, and then adding a solution, comprising: cyclopropylacetylene.

38. A process according to claim 27, wherein the stoichiometric ratios are about 3.6 equivalents of chiral moderator to about 1.5 equivalent of cyclopropylacetylene to about 3 equivalents of HMDS to about 6.1 equivalents of n-BuLi, to 1 equivalent of quinazolinone precursor.

39. A process according to claim 1, wherein the contacting is performed in the presence of an additive.

40. A process according to claim 39, wherein the additive is selected from benzene sulfonic acid, lithium benzene sulfonate, lithium trifluoromethanesulfonate (lithium triflate), 2,2,2-trifluoroethanol, (+)-camphorsulfonic acid, pyridinium p-toluenesulfonate (PPTSA), and methanesulfonic acid.

41. A process according to claim 40, wherein the additive is benzene sulfonic acid.

42. A process according to claim 41, wherein the stoichiometric ratios are about 0.15 equivalents of benzene sulfonic acid to 1 equivalent of quinazolinone.

43. A process of claim 29, wherein dehydrating is performed by heating a compound of Formula IIIa or IIIb in mesitylenes.

44. A process according to claim 29, wherein dehydrating is performed by heating a compound of Formula IIIa or IIIb in mesitylenes in the presence of a water scavenger.

* * * * *